United States Patent [19]

Cheung

[11] 4,235,044
[45] Nov. 25, 1980

[54] SPLIT STREAM METHANATION PROCESS

[75] Inventor: Harry Cheung, Buffalo, N.Y.

[73] Assignee: Union Carbide Corporation, New York, N.Y.

[21] Appl. No.: 971,815

[22] Filed: Dec. 21, 1978

[51] Int. Cl.² ............................ C10K 3/04; C10J 3/00
[52] U.S. Cl. .................................. 48/197 R; 48/210; 260/449 M
[58] Field of Search .......................... 48/197 R, 210; 260/449 M, 449.6 M

[56] References Cited

U.S. PATENT DOCUMENTS

| | | | |
|---|---|---|---|
| 3,854,895 | 12/1974 | Muller | 48/197 R |
| 3,904,389 | 9/1975 | Banquy | 48/197 R |
| 3,922,148 | 11/1975 | Child | 48/197 R |
| 3,938,968 | 2/1976 | White et al. | 48/197 R |
| 4,061,475 | 12/1977 | Moller et al. | 48/197 R |
| 4,124,628 | 11/1978 | McRobbie | 48/197 R |

OTHER PUBLICATIONS

Institute of Gas Technology Bulletin No. 31, pp. 4–7.

Primary Examiner—Peter F. Kratz
Attorney, Agent, or Firm—A. H. Fritschler

[57] ABSTRACT

A synthesis gas stream having a $H_2/CO$ ratio of less than 3/1 is split, with one stream being subjected to water gas shift essentially to completion, adjusted with a portion of the other stream to a carbon monoxide content of about 3–6% by volume, and reacted in an adiabatic methanation zone. The high hydrogen composition and high $H_2/CO$ ratio of the stream passed to the adiabatic zone is effectively regulated in this manner, preventing carbon formation and catalyst sintering. The effluent from said adiabatic zone is mixed with the remaining portion of the other stream and passed to an isothermal methanation zone. Carbon dioxide can be removed from the product methane-rich gas or from the methanation feed gas. In preferred embodiment, high pressure superheated steam is simultaneously produced by utilization of the heat of reaction of the methanation operations, enhancing the overall efficiency of the synthesis gas production-methanation operation.

32 Claims, 2 Drawing Figures

SPLIT STREAM METHANATION PROCESS

BACKGROUND OF THE INVENTION

1. Field of the Invention

The invention relates to methanation processes. More particularly, it relates to such processes having enhanced efficiency and improved operating control.

2. Description of the Prior Art

The catalytic hydrogenation of carbon monoxide is one of the most well known and established hydrogenation reactions. This reaction, which is:

$$CO + 3H_2 \rightarrow CH_4 + H_2O, \qquad (1)$$

utilizes a synthesis gas, as from the gasification of coal with oxygen and steam, that is treated to provide a desired $H_2/CO$ ratio and to remove excess $CO_2$ and deleterious impurities such as sulfur compounds. As the $H_2/CO$ ratio of the raw synthesis gas is substantially below the necessary minimum ratio of 3/1, at least a portion of the carbon monoxide in the synthesis gas is generally first reacted with steam, over iron or another suitable catalyst, in the well-known "water gas shift" reaction, as follows:

$$CO + H_2O \rightarrow CO_2 + H_2. \qquad (2)$$

Excess $CO_2$ in the gas stream is removed by conventional means, such as by treatment with alkaline absorbents. Sulfur impurities are also removed to substantially under 5 ppm, e.g. to less than about 1 ppm, preferably to less than 0.2 ppm, to protect the methanation catalyst from poisoning by such sulfur impurities.

In carrying out reaction (2), the aim is normally to shift, i.e. to make hydrogen, as far as is economically possible, with the equilibrium being determined by the reaction temperature and other operating conditions employed. Excess steam is thus employed to control the reaction temperature. The desired $H_2/CO$ ratio is obtained, to achieve maximum utilization of the available CO and hydrogen, either by very careful choice and control of the processing conditions, difficult to achieve in continuous processing operations, or by the treatment of a portion of the raw synthesis gas to produce a $H_2/CO$ ratio substantially in excess of 3/1 and blending the thus-treated gas with the untreated portion to produce the desired $H_2/CO$ ratio.

The latter approach is disclosed by the Muller patent, U.S. Pat. No. 3,854,895, which discloses dividing the gas produced by the pressure gasification of coals, and having a low $H_2/CO$ ratio, into two streams for separate treatment. One stream is subjected to water gas shift conversion, i.e. reaction (2), and subsequent carbon dioxide removal, and the other stream is not so converted. The ratio of the converted stream to the unconverted stream is between 5:1 and 1:1. The two streams are separately purified to remove sulfur and other catalyst contaminants. The residual $CO_2$ concentration of the converted stream is established at less than 3 vol.%. The $CO_2$ concentration of the converted stream is varied only slightly as a result of a small amount of absorption of $CO_2$ in the purification operation. In the water gas shift conversion preceding purification, the converted stream is adjusted to a residual CO concentration of about 4% by volume. The converted stream passing to the methanation stage is thus rich in hydrogen and poor in both CO and $CO_2$. The converted stream is passed to a first methanation reactor 30, in first methanation stage F, and thereafter to reactors 31–36 thereof in which said stream is progressively mixed with the unconverted, low $H_2/CO$ stream. Each of the reactors 31–36 is followed by condensing systems 37–42, which may include a feed water preheater and a waste heat boiler. Muller states that the ratio of the two partial streams is not varied and that the unconverted stream is divided between the reactors of methanation system F subsequent to the initial reactor 30.

Muller notes that in the temperature range of the highly exothermic methanation reaction, i.e. reaction (1), the formation of free carbon by the Boudouard reaction, that is:

$$2CO \rightarrow CO_2 + C, \qquad (3)$$

is possible and is promoted by an increasing concentration of CO in the reaction mixture. Muller also notes that formation of carbon can be suppressed by operating with a high excess of hydrogen, which assumably depresses the carbon monoxide content of the reaction mixture. If such a high excess of hydrogen is sustained throughout the methanation operation until essentially all of the carbon monoxide is fully reacted, the methane product will necessarily contain an undesirable excess of hydrogen. By operating the adiabatic methanation first reaction zone of methanation stage F with said converted stream having a large excess of hydrogen, Muller proposes to suppress carbon deposition while being able to reduce the hydrogen content of said stream by mixture with portions of the unconverted stream prior to passage to subsequent methanation reaction zones.

The first methanation stage F of Muller is an adiabatic cold feed quench reactor system in which the elevated temperatures produced by the highly exothermic methanation reaction are systematically reduced by the regulated admixture of cold feed gas. Thus, the product gas from reactor 30 is cooled, thereby generating high pressure steam, mixed with a portion of the unconverted stream, and passed to reactor 31. The remaining portion of the unconverted gas is divided and mixed with the effluent gas from all but the last reactor 36 of methanation stage F. Heat generated in each exothermic methanation zone is used to produce high pressure steam. Muller discloses three systems useful for reaction zones 31–36, namely adiabatic shaft reactors, isothermal tubular reactors, and a staged water gas shift reactor and tubular reactor. The methane produced in stage F is thereafter compressed, subjected to a final methanation trim reactor, and delivered as the product synthetic natural gas stream.

Muller suppresses carbon deposition via the Boudouard reaction on the methanation catalyst by maintaining an excess of hydrogen in the feed gas. While the kinetics of the Boudouard reaction, i.e. reaction (3), are such that negligible carbon may be formed in any event at temperatures below about 600° C. (i.e. below about 1112° F.), the reversible decomposition of methane into hydrogen and free carbon, that is $$CH_4 \rightarrow C + 2H_2 \qquad (4)$$

has been found to pose a problem at the high temperature condition of the methanation reactor effluent although not thermodynamically favored at the inlet conditions. For this reason, it is important to maintain a high relative concentration of hydrogen to methane in the high temperature adiaabatic methanation reactor effluent. This can be accomplished by maintaining a large H₂/CO ratio in the adiabatic reactor feed gas thereby assuring that sufficient hydrogen remains after methanation to prevent carbon formation by decomposition of methane product. Muller approaches this problem by attempting to avoid carbon deposition, via the Boudouard reaction, by likewise maintaining a large excess of hydrogen in the feed gas.

Another concern in the operation of a high temperature adiabatic methanation reactor is the potential for sintering of the methanation catalyst at high temperatures. The methanation reaction temperature is directly related to carbon monoxide conversion. Thus, a temperature rise of about 100° F. occurs for every 1% of carbon monoxide converted. If too much carbon monoxide is present in the first stage methanation feed, its complete conversion may generate sufficient heat to partially fuse the methanation catalyst, thereby limiting its catalytic activity. The concentration of carbon monoxide in the feed gas, therefore, must be carefully regulated. Muller, as noted above, discloses a CO content of 4%, which is within the requisite feed gas concentrations, although also relying upon the use of a cold feed quench reactor system to avoid the problem of sintering.

To regulate the H₂/CO ratio and the carbon monoxide content of the feed gas to the adiabatic reaction zone, Muller attempts to control the output of the water gas shift converter. Shift converters are typically operated with excess steam to produce an effluent gas with a low carbon monoxide content, e.g. below about 2% CO. The excess steam not only forces the equilibrium shift reaction to hydrogen and carbon dioxide products but also acts as a temperature control for the reactor. The steam serves, in effect, as an intrinsic heat sink for the exothermic shift reaction. By minimizing high temperature operation and excessive temperature excursions, a higher level of catalytic activity can be maintained in the shift reactor for longer periods of time. To suitably increase the output concentration of carbon monoxide from the water gas shift reactor to the levels required for the adiabatic methanation operation, however, Muller must employ near or below stoichiometric quantities of steam in the shift reactor. Under such conditions, a higher average operating temperature in the shift converter will result and will increase the likelihood of catalyst deactivation by sintering. Any change in catalyst activity, as by such sintering, coupled with changing water gas shift equilibrium conditions will produce fluctuations in the output of the shift converter. A fluctuating converter output can lead to catalyst sintering and carbon deposition in the subsequent methanation reaction zone when the resulting carbon monoxide concentration is high.

If, on the other hand, product carbon monoxide concentration is high and the temperature is low, metal carbonyl formation becomes a problem, particularly troublesome when an adiabatic cold feed quench reactor is employed. To overcome the problem caused by overheating, extensive recycle streams are commonly employed as diluent to adsorb some of the exothermic heat evolved. Additional measures for avoiding too high temperatures in the reactor include cooling of the catalyst bed or of the reaction gases. Local heating is difficult to avoid when internal cooling of the reactor is employed, however, and the building of internal exchange surfaces tends to be expensive. Gas recycle methods, on the other hand, require high recycle ratios, and, as a consequence, large pressure drops through the catalyst beds occur. As a result, the requirements for compressor power increase proportionately, thereby increasing compression construction costs.

There exists in the methanation art, therefore, a genuine need to avoid carbon deposition and catalyst sintering, while avoiding the necessity for excessive product gas recycle or other relatively expensive means for temperature control. In addition, the methanation operation, to be of enhanced efficiency in continuous production operations, must not be unduly sensitive to fluctuations in the water gas shift converter output as a result of declining shift catalyst activity and/or fluctuations in the CO content of the high pressure gasification effluent or other synthesis gas feed stream to the shift converter.

The adabatic cold feed quench reactor system referred to above has a low steam generation potential, which is disadvantageous with respect to the overall efficiency of an overall gasification-methanation system. Methane can typically be formed either directly in the coal gasification system or in a separate methanation system subsequent to gasification. Thermodynamically, it is more efficient to form methane in the gasifier than in a methanation system because of the higher operating temperatures possible in a coal gasification system and, accordingly, of the greater available energy. To insure significant methane production, however, the gasifier must operate at a very high pressure at which the formation of tars and heavy oils is promoted. Likewise, the problems associated with the feeding of coal solids to a high pressure environment, as well as those relating to the handling of potentially carcinogenic tars and oils, are formidable.

Lower pressure gasifiers are easier to operate and are generally advantageous, therefore, but are not as thermodynamically efficient as very high pressure gasifiers since the methanation operation must be performed in a separate methanation system subsequent to the gasification of coal or other solid carbonaceous material. A need exists in the art, therefore for improvements in the overall efficiency of lower pressure gasifier-methanator systems so as to make such systems competitive, energywise, with very high pressure gasifier systems.

It is an object of the invention to provide an improved methanation process.

It is another object of the invention to provide a process for enhancing the overall efficiency of a coal gasification-synthesis gas methanation system.

It is another object of the invention to provide a process for obviating carbon deposition and catalyst sintering in continuous methanation processes without excessive recycle of effluent gas.

It is a further object of the invention to provide an enhanced methanation process not subject to carbon deposition and catalyst sintering resulting from declining water gas shift catalyst activity and/or fluctuations in the feed gas rate in continuous production operations.

With these and other objects in mind, the invention is hereinafter described in detail, the novel features thereof being particularly pointed out in the appended claims.

SUMMARY OF THE INVENTION

Regulation and control of the carbon monoxide content of a feed gas stream to an adiabatic methanation zone are maintained in continuous operations by splitting the coal gasification product stream, or other synthesis gas, into two streams, one of which is water gas shifted essentially to completion after which a portion of the unconverted stream is added to the converted stream. In this manner, the adiabatic methanation feed gas can be maintained at a high $H_2/CO$ ratio and high hydrogen content, with the CO content within the range of about 3-6% by volume, regardless of any decline in water gas shift catalyst activity and/or fluctuations in feed gas composition. Catalyst sintering and/or carbon deposition thereon are thereby avoided, as is the necessity for employing large quantities of recycle gas. The effluent from the adiabatic methanation zone and the remainder of the unconverted gas stream are thereafter mixed and passed to an isothermal methanation zone for conversion of the remaining carbon monoxide content of the feed gas. Carbon dioxide can be removed from the system following water gas shift conversion or after the methanation operation. In either instance, embodiments of the invention utilize the exothermic heat of reaction to generate and superheat high pressure steam.

BRIEF DESCRIPTION OF THE DRAWINGS

The invention is hereinafter described with reference to the accompanying drawings in which.

DETAILED DESCRIPTION OF THE INVENTION

The objects of the invention are accomplished by a split stream methanation process in which optimum conditions within the adiabatic methanation stage can readily be maintained despite variations on the output of the water gas shift reaction zone in continuous production operations, and the exothermic heat of reaction of the methanation operation can be effectively employed to produce superheated high pressure steam. Operating difficulties such as carbon deposition and catalyst sintering in the adiabatic methanation zone are thus avoided, and the overall efficiency of coal gasification-synthesis gas methanation operations is enhanced.

In the practice of the invention, a gas rich in methane is typically produced from the product gas of a coal gasification process by (a) dividing the coal gasification product into two streams, (b) removing methanation catalyst poisons, such as sulfur compounds, from both streams, (c) converting substantially all of the carbon monoxide content of one of the streams to carbon dioxide and hydrogen by water gas shift reaction with steam, (d) adjusting the concentration of the converted steam with a portion of the other, unconverted stream in a controlled manner so as to produce a methanation stream having a carbon monoxide content of from about 3% to about 6% by volume, (e) passing the thus-adjusted methanation stream to a high temperature adiabatic methanation zone, and (f) mixing the product gas, after cooling, with the remaining unconverted stream and passing the mixture to an isothermal methanation zone. Catalyst sintering and carbon deposition in the adiabatic methanation zone are avoided. In preferred embodiments, the invention also provides for the simultaneous generation of high pressure superheated steam. In some embodiments, carbon dioxide is not removed from the methanation feed gas, but from the methane-rich product gas. In other embodiments, carbon dioxide is removed from the methanation feed gas, and at least a two stage adiabatic methanztion zone is employed, with concentration control before each stage and heat exchange thereafter as described in further detail below.

Figure 1:
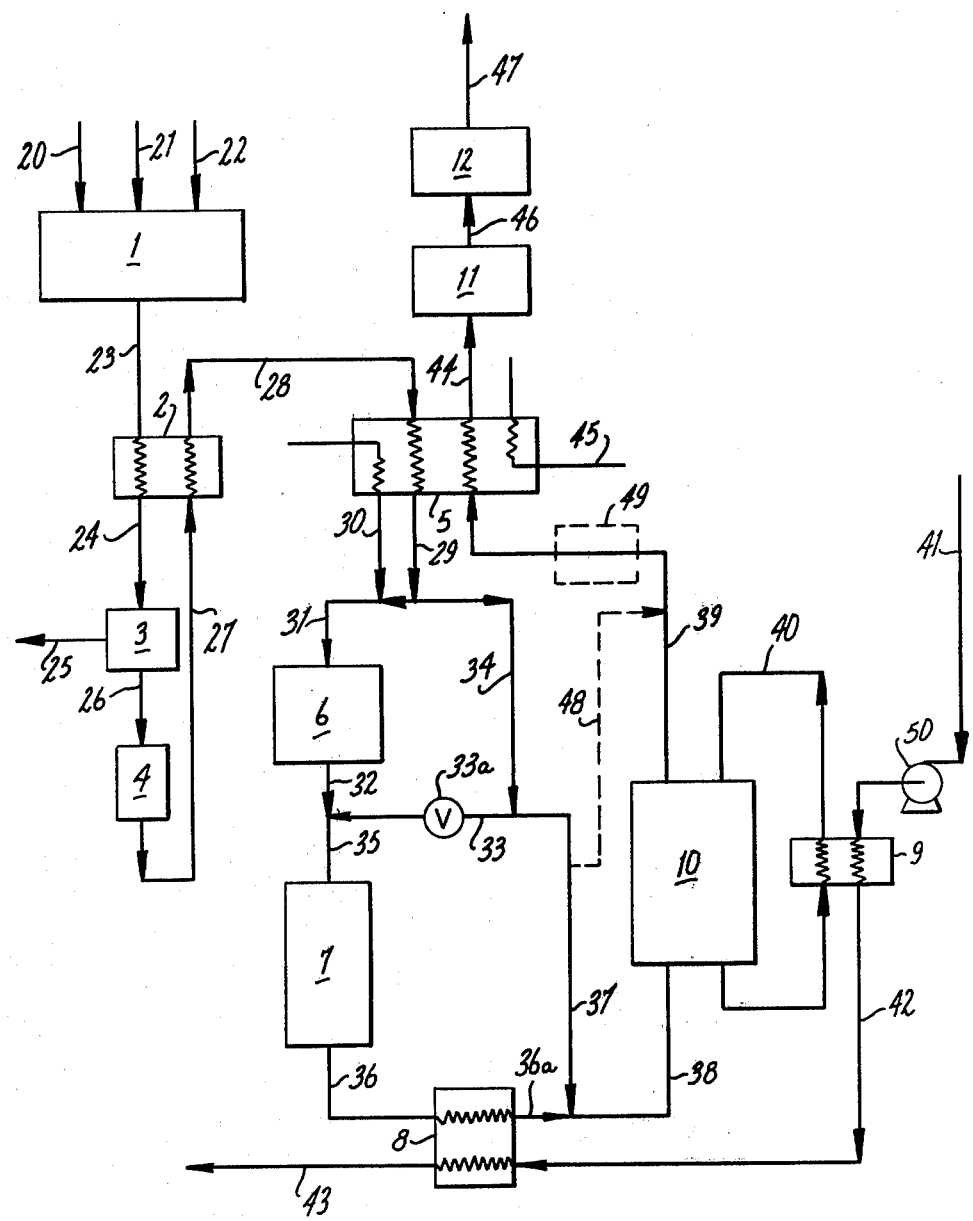
FIG. 1 is an overall process flow diagram illustrating an embodiment in which the carbon dioxide content of the gas stream being treated is removed after the methanation operation.

Referring to FIG. 1 of the drawings, coal, oxygen and steam are shown as being added to gasification zone 1 through conduits 20, 21 and 22, respectively. The effluent gasification product removed from said zone 1 through conduit 23 comprise hydrogen and carbon monoxide with various amounts of hydrocarbons, carbon dioxide, steam and sulfur compounds. The gasification product can be cooled in heat exchanger 2 against warming purified gasification product. The gasification product passes from said exchanger 2 in conduit 24 to condensation zone 3 in which condensates are separated from the gasification product and are removed through line 25. The cooled gasification product stream passes through conduit 26 to purification zone 4, in which sulfur compounds are removed from the gas stream to prevent catalyst deactivation in the subsequent methanation operation. Purification can readily be accomplished by washing with methanol at temperatures near $-30°$ C. as is known in the art. After sulfur removal, the resulting reactant gas mixture passes in conduit 27 to heat exchanger 2, as noted above, and in conduit 28 to heat exchanger 5 for further heating against cooling product gas in line 39 as hereinafter described.

Upon leaving exchanger 5 in line 29, the reaction gas stream is split or divided into two streams. One portion passes through conduit 31 and is mixed with excess steam from line 30 and is reacted essentially to completion in water gas shift reaction zone 6 in accordance with reaction (2) above. As shown, the steam in line 30 can be generated in heat exchanger 5. The other portion of the reaction gas mixture passes from conduit 29 to conduit 34 and is not passed to said shift reaction zone 6.

The composition of the effluent gas that leaves shift reaction zone 6 through conduit 32 is adjusted to between about 3% and about 6% carbon monoxide by volume by flowing a small portion of the unconverted gas stream in conduit 34 through conduit 33 and valve 33a for admixture with said converted gas stream in conduit 32. The adjusted, converted reaction gas mixture passes through conduit 35 to adiabatic reaction zone 7 as a high $H_2/CO$ and high hydrogen composition feed stream, said stream characteristics serving to effectively prevent undesired carbon formation and catalyst sintering at the high effluent temperature of adiabatic methanation zone 7. The high hydrogen to carbon monoxide ratio also serves to drive the methanation reaction, i.e. reaction (1), to near completion, making the adiabatic methanation reactor easier to control without recycling.

The hot effluent from adiabatic methanation zone 7, at a temperature on the order of about 1000° F., passes through conduit 36 to heat exchanger 8 in which it countercurrently heats saturated steam. As a result, superheated steam at a superheated level of from about 700° F. to about 950° F. is removed from heat exchanger 8 through conduit 43. The production of such superheated steam by utilization of the exothermic heat of reaction of the adiabatic methanation operation improves the overall efficiency of the gasification-methanation system. The superheated steam can conveniently be employed, as in a stream turbine for producing useful power or gas compression.

The desuperheated adiabatic methanation effluent leaves exchanger 8 in conduit 36a typically at about 550° F. and is mixed with the remaining portion of the unconverted gas stream that passes from conduit 34 to conduit 37 for admixture with the cooled adiabatic methanation effluent stream in conduit 36a. The resulting reactant gas mixture, having a hydrogen to carbon monoxide ratio of about 3, passes in conduit 38 to isothermal methanation reaction zone 10 that is kept below about 850° F. to insure high methane product composition and to prevent carbon formation. The preferred isothermal methanation reactor is a tube wall reactor, wherein the effluent gas temperature is maintained at from about 500° F. to about 850° F., preferably between about 550° F. and about 800° F. When the effluent gas temperature is maintained between about 500° F. and about 650° F., steam can be generated directly in the isothermal methanation tube reactor. When the effluent temperature is maintained between about 650° F. and about 850° F., an intermediate fluid, such as Dowtherm, is preferred to transfer the exothermic heat of the isothermal methanation reaction to a separate Dowtherm condensing steam boiling system. This system is illustrated in the drawing, with Dowtherm heat transfer fluid entering isothermal zone 10 through line 40 and being heated to a high temperature as a result of the exothermic reaction occuring therein. This heated Dowtherm stream is then exchanged with high pressure water in heat exchange zone 9. The water is passed to exchanger 9 through conduit 41 and pump 50. Steam produced in exchanger 9 or directly in isothermal zone 10 is thereafter passed through line 42 to heat exchanger 8 for superheating against the high temperature adiabatic methanation zone effluent as noted above.

The effluent gas stream from isothermal methanation reaction zone 10 is passed through line 39 to heat exchanger 5, to condense water therefrom, and is passed therefrom through line 44 to carbon dioxide removal zone 11 for removal of carbon dioxide therefrom in accordance with conventional means known in the art. A separate stream of water or other fluid can be passed through line 45 to exchanger 5 for heating therein if desired. The methane-rich product gas stream removed from zone 11 through conduit 46 comprises a synthetic natural gas, which can be compressed to the required pressure in compression zone 12, from which pressurized methane-rich product gas is withdrawn through conduit 47.

By employing an adiabatic methanation reactor rather than a cold feed quench reactor and by removing carbon dioxide after methanation rather than before, the illustrated emobdiment of the invention is able to provide for the simultaneous production of high pressure superheated steam. It is such production of high pressure superheated steam that enables the low pressure coal gasification approach to be competitive energy-wise with the very high pressure coal gasifiers in which methane is formed directly.

It is within the scope of the invention to employ a third trim methanation zone to adjust the heating value of the synthetic natural gas product. For this purpose, a small portion of the unconverted gas stream in conduit 37 is by-passed around isothermal methanation zone 10, through line 48, and is mixed with the effluent from zone 10 in line 39. This mixture is then passed to a third methanation zone, i.e. zone 49, to decrease the product hydrogen composition in the synthetic gas product. Both the initial reaction zone 7 and said third, trim methanation zone 49 are preferably adiabatic without internal cooling.

The invention will be seen to represent an improved methanation process that can be employed conveniently in the methanation of any available synthesis gas stream having an initially low $H_2/CO$ ratio of less than 3/1. Such synthesis gas streams are commonly obtained by the low pressure gasification of solid carbonaceous materials, such as coal, char and the like, with oxygen and steam. Coal gasification processes are known and available in the art, as for example the Kopper-Totzek synthesis gas production process.

It will be appreciated by those skilled in the art that the purification of the synthesis gas stream to remove sulfur compounds prior to methanation, the water gas shift and the adiabatic and isothermal methanation reactions and the carbon dioxide removal operation are all carried out generally in accordance with well know and established techniques, employing conventional catalyst materials, solvents and the like, apart from the novel features herein disclosed and claimed. While the proportions of the converted and unconverted gas streams may vary considerably depending upon the particular synthesis gas stream and operating conditions employed, the portion of the purified gasification effluent to be passed to the water gas shift conversion will generally be at least about half and up to about 85 or 90% by volume of the total gasification effluent stream split prior to methanation, with said stream to be converted commonly being about 60–70% by volume of the total purified synthesis gas to be methanated.

The water gas shift reaction, i.e. reaction (2), is preferably conducted at a temperature of about 290° C. although, with appropriate modification, can be accomplished at higher temperatures such as about 340°–370° C. The higher temperatures, however, require more steam addition than is required at lower temperatures. Although the invention is not dependent upon particular conditions being employed in the water gas shift reaction zone, a lower temperature is preferred as indicated because of the higher equilibrium constant and potential for longer catalyst life that pertains at such lower temperature level.

Figure 2:
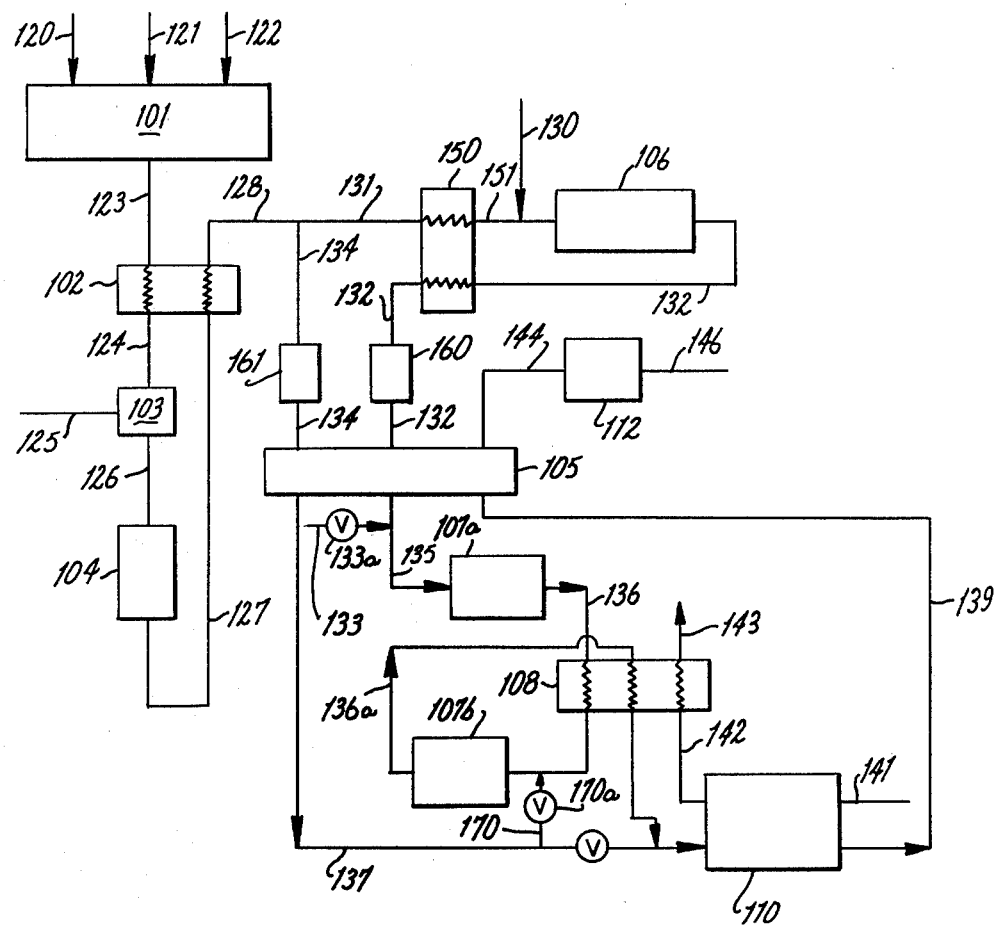
FIG. 2 is an overall process flow diagram illustrating an alternate embodiment in which carbon dioxide removal from the gas stream occurs before the methanation operation.

FIG. 2 illustrates an alternate embodiment in which carbon dioxide is removed prior to methanation. Coal, oxygen and steam are added to gasification zone 101 through conduits 120, 212, and 122, respectively. The effluent gasification product removed from zone 101, comprising a synthesis gas stream having a low $H_2/CO$ ratio of less than 3/1, again typically contains hydrogen and carbon monoxide with various amounts of hydrocarbons, carbon dioxide, steam and sulfur compounds. This stream passes through conduit 123 to heat exchanger 102, where it can be cooled against warming purified gasification product. The cooled gas steam leaves exchanger 102 through conduit 124 and passes to condensation zone 103 in which condensates are separated from the gas steam and removed through line 125. The cooled gas stream then passes through conduit 126 to purification zone 104 in which sulfur compounds are removed therefrom by conventional means to prevent catalyst deactivation in the subsequent methanation reactors, e.g., by washing with methanol at temperatures near $-30°$ C. Following such sulfur removal, the purified reactant gas mixture passes in conduit 127 to heat exchanger 102 where it is warmed against cooling gasification product as previously noted. The warmed reactant gas mixture having a $H_2/CO$ ratio of less than 3/1 leaves exchanger 102 through line 128 and is split, with the first, generally larger stream passing to conduit 131 for eventual passage to water gas shift conversion and methanation. The second stream passes to conduit 134 for eventual use in accordance with the invention as an unconverted gas stream having a $H_2/CO$ ratio of less than 3/1.

The first stream in conduit 131 is warmed in heat exchange zone 150 against the cooling water gas shift reactor product referred to below and, after warming, leaves zone 150 in conduit 151, is mixed with excess steam from line 130 and passes to water gas shift reaction zone 106. The reactant gas-steam mixture is reacted essentially to completion in zone 106 in accordance with reaction (2) above. The effluent or product gas from said zone 106 passes through line 132 to heat exchanger 150, as noted above, and upon such cooling continues in line 132 to purification zone 160, heat exchanger 105 and adiabatic reactor 107a.

The cooled, converted gas stream in line 132 passes to purification zone 160 for carbon dioxide removal by conventional means, while said second stream similarly passes in line 134 to purification zone 161 for carbon dioxide removal therein. In purification zones 160 and 161, carbon dioxide can be removed by such conventional processes as the Benfield potassium carbonate wash, the Fluor Solvent Wash, the Rectisol process or other commercially available carbon dioxide removal processes. After carbon dioxide removal, the converted gas stream in line 132 and the unconverted gas stream in line 134 are both heated in heat exchanger 105 against cooling methane-rich product gas in line 139.

Upon leaving heat exchanger 105, the converted gas stream in line 132 is then adjusted to between from about 3% and about 6% carbon monoxide content by volume, the resulting converted, adjusted gas stream in line 135 having a high hydrogen to carbon monoxide ratio and a high composition of hydrogen. This adjustment is accomplished by flowing a small portion of the unconverted gas stream leaving heat exchanger 105 in line 137 through conduit 133 and valve 133a therein to said line 135 for mixture with and adjustment of the converted gas stream in line 135.

The adjusted gas stream in line 135 passes to first stage adiabatic reactor 107a, in which reaction (1) occurs, and in which carbon formation and catalyst sintering are avoided by the high hydrogen composition and high $H_2/CO$ ratio of the adjusted gas stream. The hot effluent from adiabatic reaction zone 107a containing methane, steam and excess hydrogen leaves said zone in conduit 136 at a temperature on the order of 1000° F. and is passed to heat exchanger 108 in which it is cooled by countercurrently superheating saturated steam, which is removed from exchanger 108 through conduit 143 at a temperature typically in the range of from about 700° F. to about 950° F. This superheated steam can be employed in a steam turbine for producing useful power or gas compression.

The desuperheated adiabatic methanation reactor first stage effluent in conduit 136 is at about 550° F. upon leaving exchanger 108. This stream is, in the illustrated embodiment, again adjusted by mixture with a small portion of the unconverted gas stream in line 137 to provide a reactant gas mixture having a carbon monoxide content of from about 3% to about 6% by volume. This is accomplished by passing a very small portion of the unconverted stream in line 137 through conduit 170 and valve 170a therein to conduit 136 for mixture with the effluent gas from the first stage adiabatic methanation zone 107a. The newly adjusted reactant mixture, having a $H_2/CO$ ratio of greater than 3/1 and a relatively high hydrogen composition is passed to second stage adiabatic methanation zone 107b for further methanation in accordance with reaction (1). The effluent from said zone 107b, containing product methane, steam and excess hydrogen, passes through line 136a to heat exchanger 108, in which it is cooled, together with the effluent from first stage zone 107a, by countercurrently superheating saturated steam.

In the illustrated embodiment, the prior removal of carbon dioxide leads to the employment of the two adiabatic methanation stages or zones 107a and 107b. When handling a synthesis gas such as the effluent of a Koppers-Totzek gasifier, there is generally not sufficient heat capacity in the adiabatic methanation product, absent said carbon dioxide, to superheat all of the steam generated in the subsequent isothermal methanation system as in the embodiment illustrated in FIG. 1. By employing a second adiabatic methanation zone as in the FIG. 2 embodiment, additional heat is available to accomplish the desired superheating, thereby enhancing the overall efficiency of the gasification-methanation operation.

After the effluent from the second adiabatic methanation zone is cooled in heat exchanger 108, it is mixed with the remaining portion of the unconverted stream in line 137 to provide a reactant mixture having a hydrogen to carbon monoxide ratio of about 3/1, this mixture being passed to isothermal methanation reaction zone 110 in which essentially all of the carbon monoxide is converted to methane. The isothermal methanation reactor effluent is kept below about 850° F. to insure high methane product composition and to prevent carbon formation and deposition on the catalyst in said zone.

The preferred isothermal methanation reactor is a tube wall reactor in which the effluent gas temperature is maintained between about 500° F. and 850° F., preferably between about 550° F. and 800° F. In the illustrated embodiment of FIG. 2, the effluent gas temperature is conveniently maintained between about 550° F. and 650° F., so that steam can be generated directly in the tube wall reactor 110 from water in line 141, with the resulting steam passing from reactor 110 through line 142 to heat exchanger 108 for superheating therein as noted above.

The effluent gas stream from isothermal reaction zone 110 is passed through conduit 139 to heat exchanger 105 for cooling therein, to condense water therefrom. The methane-rich product gas stream is then passed to compression system 112 from which high pressure product gas, constituting a synthetic natural gas, is withdrawn through line 146.

It will be understood that various changes and modifications can be made in the embodiment of FIG. 2, and in the other embodiments, without departing from the scope of the invention as disclosed and claimed herein. In the FIG. 2 embodiment, a trim methanation reactor may be employed and incorporated into the process in the manner disclosed with reference to the FIG. 1 embodiment. It is also within the scope of the invention to employ one or more additional methanation zones in addition to those shown in FIG. 2, with the feed stream to each such additional zone be adjusted with a portion of the unconverted gas stream to a CO content of about 3–6% by volume, and the effluent thereof being cooled as in heat exchanger 108, to effectively utilize the exothermic heat of reaction of the adiabatic methanation zones to superheat steam such as that generated by the heat of reaction of the isothermal methanation reaction zone. As the isothermal zone is maintained at a temperature of from about 500° F. to about 850° F., those skilled in the art will appreciate that the effluent stream removed from the adiabatic reaction zone, typically at a temperature on the order of about 1000° F., is conveniently cooled to from about 500° F. to about 850° F. prior to being mixed with the remaining portion of the second processing stream, with said effluent being typically cooled to about 550° F. as indicated above.

The invention is further described with reference to the following illustrative examples that are not to be construed as limiting the scope of the invention as recited in the appended claims.

EXAMPLE 1

A synthesis gas produced by the Koppers-Totzek gasification process utilizing one ton of Eastern coal having a sulfur content of about 3% by weight comprises 67,500 scf (standard cubic feet at 70° F. and 1 atm.) of product gas with the approximate composition of Table I below.

TABLE I

| Component | % by Volume |
|---|---|
| CO | 54.5% |
| $CO_2$ | 7.0 |
| $H_2$ | 36.3 |
| $N_2$ | 0.7 |
| $H_2S/COS$ | 1.0 |
| $H_2O$ | 0.3 |

This gas is compressed to about 11 atm. and is then processed in accordance with the embodiment of FIG. 1 wherein it is first cooled to remove condensibles and then processed in a sulfur purification zone 4 to yield 65,690 scf of gas having the approximate composition set forth in Table II below.

TABLE II

| Component | % by Volume |
|---|---|
| CO | 56.0% |
| $CO_2$ | 6.0 |
| $H_2$ | 37.3 |
| $N_2$ | 0.7 |

This gas is then split into two streams, with 41,250 scf passing into conduit 31 and the remaining 24,440 scf being diverted into conduit 34. The gas in conduit 31 is mixed each 2,180 lb. of 160 psia saturated steam introduced through conduit 30, and the gas mixture so produced is reacted in the water gas shift reaction zone 6 to yield 84,700 scf of gas in conduit 32, said gas having the approximate composition illustrated in Table III.

TABLE III

| Component | % by Volume |
|---|---|
| CO | 1.7% |
| $CO_2$ | 28.5 |
| $H_2$ | 43.8 |

TABLE III-continued

| Component | % by Volume |
|---|---|
| $N_2$ | 0.4 |
| $H_2O$ | 25.6 |

The composition of this stream is then adjusted with 3,700 scf of the unconverted stream introduced through conduit 33 and valve 33a therein to raise the carbon monoxide concentration to about 3.9% in conduit 35. This stream is then reacted in the adiabatic methanation reactor 7 to a temperature near 1000° F., thereby producing 81,600 scf of gas with the approximate composition listed in Table IV below. This gas is used to superheat about 4,000 lb. of 1200 psia saturated steam to about 920° F. in heat exchanger 8. The saturated steam so heated is that produced in the low temperature methanation zone.

TABLE IV

| Component | % by Volume |
|---|---|
| CO | 0.1% |
| $CO_2$ | 29.9 |
| $H_2$ | 34.7 |
| $N_2$ | 0.4 |
| $H_2O$ | 30.8 |
| $CH_4$ | 4.2 |

The superheated adiabatic methanator effluent in conduit 36a is then mixed with the remainder of the unconverted stream in conduit 37, and the mixture is introduced into isothermal methanation reaction zone 10 through conduit 38. In said reaction zone 10, the hydrogen and carbon monoxide are reacted essentially to completion to yield about 79,000 scf of gas with the approximate composition listed in Table V below. The exothermic heat of reaction released in isothermal reaction zone 10 maintained at less than 850° F. is used to produce 1200 psia saturated steam.

TABLE V

| Component | % by Volume |
|---|---|
| CO | 0.04% |
| $CO_2$ | 32.4 |
| $H_2$ | 1.4 |
| $N_2$ | 0.6 |
| $H_2O$ | 46.5 |
| $CH_4$ | 19.0 |

The gas is further cooled in heat exchanger 5, after which carbon dioxide is removed in zone 11 and 17,000 scf of product gas having the approximate composition listed in Table VI below is compressed to about 75 atm. in compression zone 12.

TABLE VI

| Component | % by Volume |
|---|---|
| CO | 0.2% |
| $CO_2$ | 1.5 |
| $H_2$ | 6.6 |
| $N_2$ | 2.8 |
| $H_2O$ | 0.2 |
| $CH_4$ | 88.7 |

The product synthetic natural gas stream is removed through conduit 47.

EXAMPLE 2

The illustrative example is based on the gasification product gas referred to in Example 1 and identified on Table I. The gas is subjected to the same cooling and sulfur purification steps as in Example 1 to yield 65,690 scf of gas with the approximate composition set forth in Table II. This gas stream is split into two streams with 41,070 scf of gas passing into conduit 131 with the remaining 24,620 scf of gas being diverted into conduit 134, for treatment and use in accordance with the illustrated embodiment of FIG. 2. The gas in conduit 131 is mixed with 2,170 lb. of 160 psia saturated steam introduced through conduit 130, and the gas mixture so produced is reacted in the water gas shift reaction zone 106 to yield 84,300 scf of gas in conduit 132, said gas having the approximate composition set forth in Table VII.

TABLE VII

| Component | % by Volume |
|---|---|
| CO | 1.6% |
| $CO_2$ | 28.6 |
| $H_2$ | 43.8 |
| $N_2$ | 0.4 |
| $H_2O$ | 25.7 |

The converted stream is then cooled in heat exchanger 150 to remove water therefrom. The converted stream and the unconverted stream are treated in zones 160 and 161, respectively, to remove the bulk of the carbon dioxide therefrom. The compositions of the resulting streams in conduits 132 and 134, the converted and unconverted streams, respectively, are as set forth in Table VIII.

TABLE VIII

| Component | % by Volume Stream 132 | % by Volume Stream 134 |
|---|---|---|
| CO | 3.2% | 59.3% |
| $CO_2$ | 0.4 | 0.4 |
| $H_2$ | 88.6 | 39.5 |
| $N_2$ | 0.7 | 0.8 |
| $H_2O$ | 9.1 | — |

The composition of stream 132 is then adjusted with 337 scf of the unconverted gas stream introduced through conduit 133 and valve 133a to raise the carbon monoxide concentration to about 3.6% by volume in conduit 135. This stream is then reacted in adiabatic methanation reaction zone 170a to a temperature near 1000° F., thereby producing 40,030 scf of gas having the approximate composition recited in Table IX below. This gas is used to superheat, in part, saturated steam produced in the low temperature methanation zone in heat exchanger 108.

TABLE IX

| Component | % by Volume |
|---|---|
| CO | 0.2% |
| $CO_2$ | 0.4 |
| $H_2$ | 81.4 |
| $N_2$ | 0.7 |
| $H_2O$ | 13.6 |
| $CH_4$ | 3.7 |

The desuperheated adiabatic methanation reaction zone first stage effluent in conduit 136 is again adjusted with 2528 scf of the unconverted gas stream introduced through conduit 170 and valve 170a to raise the carbon monoxide concentration to about 3.7% prior to the second stage 107b of the adiabatic methanation reaction zone. This mixture is then reacted in adiabatic methanation reaction zone second stage 107b to a temperature near 1,000° F., thereby producing about 39,800 scf of gas having the approximate concentration listed in Table X below. This gas is used to produce the remaining heat necessary to superheat the saturated steam produced in the lower temperature isothermal methanation zone in heat exchanger 108. About 3,450 lb. of 1200 psia steam superheated to 960° F. is produced in this manner.

TABLE X

| Component | % by Volume |
|---|---|
| CO | 0.1% |
| $CO_2$ | 0.4 |
| $H_2$ | 73.0 |
| $N_2$ | 0.8 |
| $H_2O$ | 18.1 |
| $CH_4$ | 7.6 |

The desuperheated adiabatic methanation reaction zone second stage effluent in conduit 136a is then mixed with the remainder of the unconverted stream from conduit 137 and the mixture is introduced into the isothermal methanation reaction zone 110. In reaction zone 110, the hydrogen and carbon monoxide are reacted essentially to completion to yield about 38,118 scf of gas in conduit 139 having the approximate composition listed under the indicated column in Table XI. The heat released in reaction zone 110, maintained at less than 850° F., is used to produce 1200 psia of saturated steam. The product gas is further cooled in heat exchanger 105 and is compressed to about 75 atm. in compression zone 112 to yield an SNG product gas in conduit 146 having the approximate composition listed in the indicated column of Table XI.

TABLE XI

| Component | % by Volume Stream 139 | % by Volume Stream 146 |
|---|---|---|
| CO | 0.1% | 0.2% |
| $CO_2$ | 0.7 | 1.5 |
| $H_2$ | 2.0 | 4.7 |
| $N_2$ | 1.2 | 2.8 |
| $H_2O$ | 56.3 | 0.1 |
| $CH_4$ | 39.7 | 90.7 |

It will be appreciated that the invention may be employed with any suitable commerically available catalyst material, and that various alternatives or modifications can be made within the scope of the invention. The removal of sulfur components is a conventional processing step employed with regard to typical gasification product streams because of the presence of sulfur components therein to an extent sufficient to have a deleterious effect on many commonly employed methanation catalysts. To the extent that a particular gasification product stream may not have a significant amount of such sulfur components, or in the event a particular methanation catalyst may be able to tolerate the level of sulfur components present, the sulfur purification step can be omitted.

In its broad processing aspects, the invention provides for practical and highly significant improvements in the methanation art. The invention enables methanation conditions to be readily employed, regulated and controlled so that undesired carbon deposition and sintering can be avoided. The invention is not susceptible to disruption in continuous production operations, as for example by a decline in the activity of the preliminary water gas shift catalyst and/or fluctuations in the gasification product composition in continuous production operations, thereby being particularly applicable in commercial methanation operations. By effectively utilizing the exothermic heat of reaction of the methanation reactions to generate and superheat steam, the invention enhances the overall efficiency of gasification-methanation operations. In view of the continuing need for the development of more economic processes for the production of SNG products as a part of overall efforts to meet the energy needs of modern industrial societies, the invention is of particular importance in light of the ever-increasing awareness and concern as to the availability of practical energy sources on a long term, commercially feasible basis.

What is claimed is:

1. An improved process for the methanation of synthesis gas comprising:
   (a) dividing a synthesis gas stream containing hydrogen and carbon monoxide and having an $H_2/CO$ ratio of less than 3/1 into two separate processing streams;
   (b) reacting the first of said separate processing streams essentially to completion with steam in a water gas shift zone, thereby producing a converted gas stream containing carbon dioxide and hydrogen;
   (c) adding a portion of the second, unconverted, separate processing stream to said converted gas stream to produce an adjusted gas stream having a carbon monoxide content of from about 3% to about 6% by volume, said adjusted gas stream having a high $H_2/CO$ ratio in excess of 3/1 and a high hydrogen content;
   (d) adiabatically reacting said adjusted gas stream in a high temperature adiabatic reaction zone to form an effluent gas stream containing methane, excess hydrogen and steam, said effluent gas stream having a temperature on the order of about 1000° F.;
   (e) cooling said effluent gas stream from the adiabatic reaction zone by passing said stream in heat exchange with high pressure steam, said effluent gas stream being cooled to from about 500° F. to about 850° F. and thereby producing high pressure superheated steam;
   (f) mixing said cooled effluent gas stream and the remaining portion of said second, unconverted, separate processing stream to form a reaction mixture having a $H_2/CO$ ratio on the order of 3/1;
   (g) passing said reaction mixture to an isothermal methanation zone maintained at a methanation temperature of from about 500° F. to about 850° F., essentially all of the carbon monoxide present in said reaction zone being converted to methane; and
   (h) cooling the methane-rich effluent gas stream from said isothermal zone in a condensation zone to condense water therefrom, whereby methane can be produced without undesired catalyst sintering and carbon deposition in the high temperature adiabatic reaction zone, said CO adjustment enabling the CO concentration in said reaction zone to be readily maintained in continuous production operations despite variations in the CO output of the shift zone as a result of catalyst aging and/or fluctuations in the feed gas stream to said shift zone, the high hydrogen to carbon monoxide ratio serving also to drive the adiabatic methanation reaction to near completion and obviating the need for extensive recycle of the effluent from the adiabatic methanation zone, the production of high pressure superheated steam enhancing the efficiency of the overall synthesis gas-methanation production operation.

2. The process of claim 1 in which said isothermal zone is maintained at a temperature of from about 500° F. to about 650° F.

3. The process of claim 1 in which said high pressure steam passed in heat exchange with the high temperature effluent from the adiabatic zone comprises high pressure steam generated from the heat produced in said isothermal zone.

4. The process of claim 1 in which the temperature of the effluent gas stream from the isothermal zone is maintained at from about 500° F. to about 650° F., said steam being generated directly in the isothermal reaction zone.

5. The process of claim 1 in which the temperature of the effluent gas stream from the isothermal zone is maintained at from about 650° F. to about 850° F., and including the heating of an intermediate fluid to transfer the exothermic heat of reaction from said isothermal zone to a heat exchange zone in which high pressure water is converted to steam by heat exchange with said intermediate fluid.

6. The process of claim 1 in which the synthesis gas stream is produced by the gasification of solid carbonaceous material.

7. The process of claim 6 in which said solid carbonaceous material is coal.

8. The process of claim 1 in which the separate processing stream that is subjected to water gas shift comprises more than about 50% of the synthesis gas stream divided into two separate processing streams.

9. The process of claim 8 in which said separate processing stream subjected to water gas shift comprises from about 50% to about 90% of said synthesis gas stream.

10. The process of claim 1 and including passing said synthesis gas stream to a purification zone for the removal of sulfur compounds therefrom prior to dividing said stream into two separate processing streams, the removal of such sulfur compounds preventing catalyst deactivation thereby in the subsequent reaction zones.

11. The process of claim 1 and including removing carbon dioxide from the gas being processed, the methane-rich effluent gas stream constituting a synthetic natural gas product.

12. The process of claim 1 and including passing said converted gas stream and said second, unconverted, separate processing stream to carbon dioxide purification zones for the removal of carbon dioxide therefrom, prior to the addition of a portion of said second stream to said converted stream, the methane-rich effluent gas stream removed from said condensation zone constituting a synthetic natural gas product.

13. The process of claim 12 and including (1) cooling said effluent gas stream from the adiabatic reaction zone in heat exchange with steam; (2) mixing said cooled effluent gas stream with an additional portion of said second, separate processing stream to provide a second adjusted gas stream having a carbon monoxide content of from about 3% to about 6% by volume, said second adjusted gas stream having a high $H_2/CO$ ratio in excess of 3/1 and a high hydrogen content; (3) adiabatically reacting said second adjusted gas stream in a second high temperature adiabatic reaction zone to form a second effluent gas stream containing methane, excess hydrogen and steam, and (4) cooling said second effluent gas stream in heat exchange with steam, thereby producing high pressure superheated steam by said heat exchange with said effluent streams, said cooled second effluent gas stream being said effluent stream mixed with the remaining portion of said second, separate processing stream and passed to said isothermal methanation zone.

14. The process of claim 13 and including mixing said cooled second effluent gas stream with at least one further additional portion of said second, separate processing stream to provide at least one additional adjusted gas stream having a carbon monoxide content of at least about 3% to about 6% by volume, said additional adjusted gas streams having a high $H_2/CO$ ratio in excess of 3/1 and a high hydrogen content; and adiabatically reacting each said additional adjusted gas streams in additional high temperature adiabatic reaction zones to form additional effluent gas streams containing methane, excess hydrogen and steam, the last said additional effluent gas stream being the effluent stream mixed with the remaining portion of said second, separate processing stream and passed to said isothermal methanation zone.

15. The process of claim 13 in which the steam passing in heat exchange with said effluent gas stream from the adiabatic reaction zone and with said second effluent gas stream from second adiabatic reaction zone is steam generated from the heat produced in said isothermal zone.

16. The process of claim 15 in which the temperature of the effluent stream from said second adiabatic reaction zone is on the order of about 1000° F., said stream being cooled to from about 500° F. to about 850° F. prior to being mixed with unconverted gas from said second stream.

17. The process of claim 16 in which said isothermal zone is maintained at a temperature of from about 500° F. to about 650° F.

18. The process of claim 17 in which said steam is generated directly in the isothermal reaction zone.

19. The process of claim 21 in which the temperature of the effluent gas stream from the isothermal zone is maintained at from about 650° F. to about 850° F., and including the heating of an intermediate fluid to transfer the exothermic heat of reaction from said isothermal zone to a heat exchange zone in which high pressure water is converted to steam by heat exchange with said intermediate fluid.

20. The process of claim 12 in which the synthesis gas stream is produced by the gasification of solid carbonaceous material.

21. The process of claim 20 in which said solid carbonaceous material is coal.

22. The process of claim 12 in which the separate processing stream subjected to water gas shift comprises more than about 50% of the synthesis gas stream divided into two separate processing streams.

23. The process of claim 13 in which the separate processing stream subjected to water gas shift comprises more than about 50% of the synthesis gas stream divided into two separate processing streams.

24. The process of claim 23 in which said separate processing stream subjected to water gas shift comprises from about 50% to about 90% of said synthesis gas stream.

25. The process of claim 13 and including passing said synthesis gas stream to a purification zone for the removal of sulfur compounds therefrom prior to dividing said stream into two separate processing streams, the removal of said sulfur compounds preventing catalyst deactivation thereby in the subsequent reaction zones.

26. The process of claim 13 and including passing the effluent gas stream from said isothermal zone to a further methanation zone to decrease the hydrogen content of the methane-rich product gas stream, a small portion of said second, unconverted separate processing stream by-passing said isothermal reaction zone and being passed to said further methanation zone, the effluent gas from which comprising the methane-rich stream passed to said condensation zone.

27. The process of claim 26 in which said further methanation zone comprises an adiabatic reaction zone.

28. The process of claim 1 and including removing carbon dioxide from said cooled methane-rich effluent gas stream, the thus-treated effluent gas stream constituting a synthetic natural gas product.

29. The process of claim 28 in which the synthesis gas stream is produced by the gasification of solid carbonaceous material.

30. The process of claim 29 in which said carbonaceous material is coal.

31. The process of claim 28 in which the separate processing stream subjected to water gas shift comprises more than about 50% of the synthesis gas stream divided into two separate processing streams.

32. The process of claim 28 and including passing said synthesis gas stream to a purification zone for the removal of sulfur compounds therefrom prior to dividing said stream into two separate processing streams, the removal of said sulfur compounds preventing catalyst deactivation thereby in the subsequent reaction zones.

* * * * *